United States Patent [19]

Køhnke et al.

[11] 4,453,543

[45] Jun. 12, 1984

[54] ANAESTHESIA—BREATHING APPARATUS

[75] Inventors: Ole B. Køhnke, Vattholma, Sweden; Henning Ruben, Skodsborg, Denmark

[73] Assignee: Testa-Laboratorium A/S, Copenhagen, Denmark

[21] Appl. No.: 373,509

[22] PCT Filed: Aug. 31, 1981

[86] PCT No.: PCT/SE81/00243

§ 371 Date: Apr. 20, 1982

§ 102(e) Date: Apr. 20, 1982

[87] PCT Pub. No.: WO82/00766

PCT Pub. Date: Mar. 18, 1982

[30] Foreign Application Priority Data

Sep. 1, 1980 [SE] Sweden .................. 8006085

[51] Int. Cl.³ ............................ A61M 16/00
[52] U.S. Cl. ................ 128/203.28; 128/204.25; 128/205.12; 128/205.17; 128/205.24; 128/911
[58] Field of Search .......... 128/203.28, 204.25, 128/205.13, 205.15, 205.16, 205.17, 205.12, 205.19, 910, 911

[56] References Cited

U.S. PATENT DOCUMENTS 3,200,818 8/1965 Johannisson .................. 128/205.17
3,700,000 10/1972 Hesse et al. .
3,814,091 6/1974 Henkin .
3,901,230 8/1975 Henkin .
4,007,737 2/1977 Paluch ..................... 128/911

FOREIGN PATENT DOCUMENTS 122712 4/1972 Denmark .
2331188 1/1974 Fed. Rep. of Germany .
1224367 6/1960 France .
7308537-5 6/1973 Sweden .

Primary Examiner—Henry J. Recla
Attorney, Agent, or Firm—Spencer & Frank

[57] ABSTRACT

An anaesthesia-breathing apparatus for supplying gas to a patient for artificial respiration, supported respiration, anaesthesia purposes or combinations of such purposes. The apparatus comprises a gas chamber connected to a patient connection piece, a respiratory gas receptacle, for example in the form of a respiration bag, a first check valve adapted to permit discharge of excess gas from the breathing apparatus to the atmosphere and, optionally a filter for absorption of carbon dioxide from recirculation breathing gas. Security and venting valves are not required for the patient's security during manual operation of the respiration bag because the gas chamber is in communication with the patient connecting piece via a control valve which alternately conducts exhaled gas to one end of a recirculation gas chamber or closes the communication to the recirculation gas chamber and conducts the exhaled gas from the gas chamber to the patient. The recirculation gas chamber, which holds at least the volume of gas exhaled by a mature person that has been in contact with the lung alveoli, is connected at its other end via a second check valve opening towards the respiratory gas receptacle, to the respiratory gas receptacle. A side duct, which is in communication with the atmosphere via the first check valve, is connected to the recirculation gas chamber near the one end, and a connection for supplying fresh gas from a pressurized source opens into the recirculation gas chamber immediately upstream from the second check valve.

8 Claims, 7 Drawing Figures

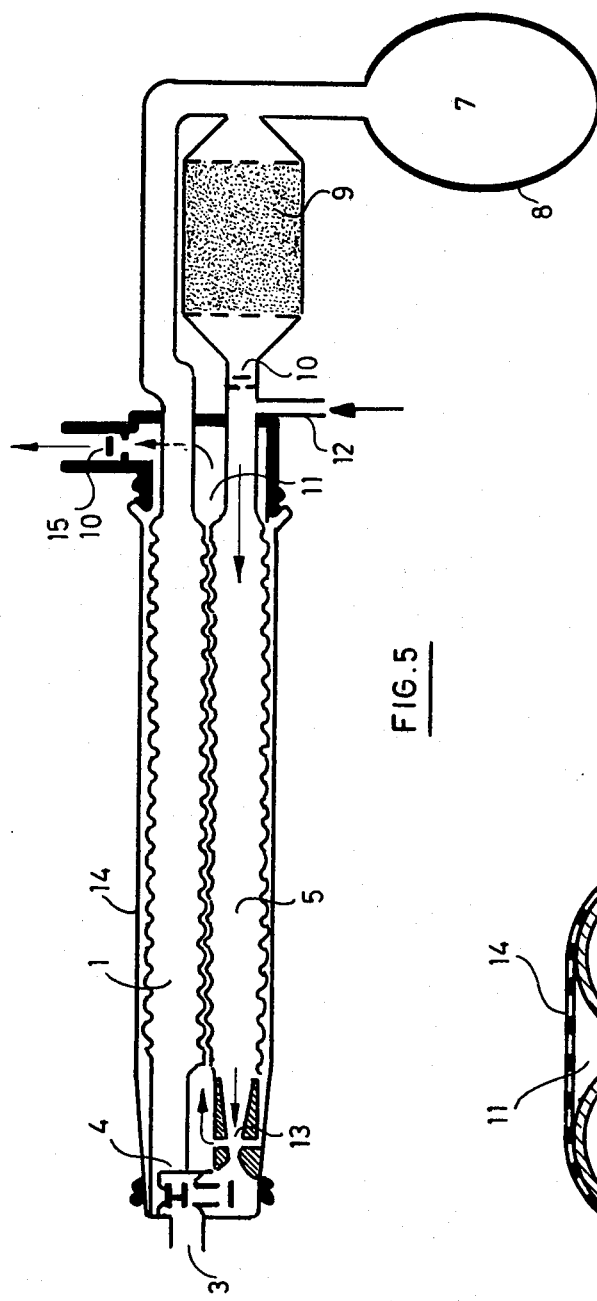
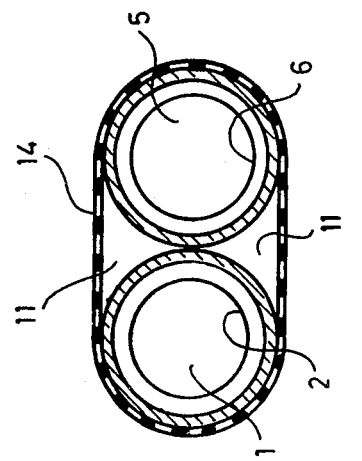
FIG. 5
FIG. 6

ANAESTHESIA—BREATHING APPARATUS

BACKGROUND OF THE INVENTION

The object of the invention is to provide an anaesthesia-breathing apparatus by means of which gas can be supplied to a patient for artificial respiration, supported respiration, anaesthesia purposes or combinations of such purposes. Such apparatuses which for example are known from Swedish published specification 7308537-5 or U.S. Pat. Nos. 3,814,091 and 3,901,230 comprises a gas chamber connected, on the one hand, to a patient connecting piece and, on the other hand, a respiratory gas receptacle, for example in the form of a respiration bag, a check valve adapted to permit discharge of excess gas from the breathing apparatus to the atmosphere and, optionally, a filter for absorption of carbon dioxide from recirculating breathing gas.

Most closely related with the object of the invention as far as the function is concerned is the anaesthesia-breathing apparatus according to the above-mentioned U.S. Pat. Nos. 3,814,091 and 3,901,230. The apparatus shown fundamentally in FIG. 3 of U.S. Pat. No. 3,901,230 operates substantially in the same way as the apparatus according to the present invention in those cases in which the patient is breathing spontaneously. Both apparatuses operate in this case according to the well-known Magill-narcosis-breathing system. However, use of the known apparatus is used for performing controlled ventilation, or supported ventilation which is a transition form between spontaneous respiration and controlled ventilation, the known has drawbacks which may be dangerous for the patient. In all the embodiments described in U.S. Pat. No. 3,901,230 a closure of the gas discharge valve can take place when the breathing bag is manually operated. If this happens the system is filled with fresh gas causing the pressure to increase. For this reason the provision of a security valve in this system is required in order to prevent the build-up of dangerously high pressures in the lungs of the patient in consequence of the gas supply. In addition the known apparatus requires the provision of a venting valve which upon manual operation permits discharge of gas from the excessively filled system to permit the state of locking to be removed.

SUMMARY OF THE INVENTION

Apparatus constructed in accordance with the present invention completely removes these and other drawbacks by a construction in which the gas chamber is in connection with the patient connecting piece via a control valve which alternately conducts exhaled gas to one end of a recirculation gas chamber or closes the connection to the recirculation gas chamber and conducts the exhaled gas from the gas chamber to the patient. The recirculation gas chamber, which at least holds the volume of gas exhaled by a mature person that has been in contact with the lung alveoli, at its other end is connected, via a second check valve opening towards the respiratory gas receptacle, to the respiratory gas receptacle. A side duct, which is in connection with the atmosphere via a first check valve, is connected to the recirculation gas chamber near said one end, while a connection for supplying fresh air from a pressurized source opens into the recirculation gas chamber immediately upstream from the second check valve.

If an apparatus having these characteristic features is used by a patient whose breathing function is paralyzed and which thus must be supplied controlled or at least supported ventilation, the control valve and the second check valve cooperate in such a way that during the inhalation phase, when the respiration bag is compressed, an independent recirculation gas chamber is defined in such a way that the inflating pressure cannot enter therein. As the fresh-gas supply and the first check valve, i.e. the discharge valve, both are in connection with the recirculation gas chamber as defined, the following advantageous properties which are not achievable with the apparatuses known so far, are obtained in the present apparatus:

1. No adjustment of the first check valve is required during transition between spontaneous respiration and controlled ventilation (increased-pressure ventilation).

2. The supply of fresh gas cannot produce a pressure in the system in excess of the opening pressure of the first check valve, that is, discharge valve.

3. The opening pressure of the discharge valve, i.e. the first check valve, can be chosen at a very low value.

4. Under no circumstances can an undesirable closure of the discharge valve occur due to the flow conditions in the flow circuit or due to the operation of the respiration bag.

5. The fresh gas can displace the alveolar expiration gas from the system not only during the last part of the exhalation phase after the respiration bag has become filled, but also during the whole inhalation phase. This means that the apparatus permits an "orderly" displacement of the alveolar expiration gas present in the recirculation gas chamber during an extended period in comparison with the apparatus described in the above-mentioned U.S. patent where only the last part of the expiration period is disposable for this purpose. At a given adjustment of the fresh-gas supply the apparatus according to the invention accordingly will displace alveolar gas at a highly increased efficiency which means improved fresh-gas economy.

In a particularly advantageous embodiment of the invention the recirculation gas chamber near the control valve has the shape of a convergent-divergent duct, the side duct being connected to the recirculation gas chamber at the most constricted portion of the convergent-divergent duct.

BRIEF DESCRIPTION OF THE DRAWINGS

The above-mentioned and other embodiments of the object of the invention as well as the operation of the apparatus are explained hereafter by reference to the attached drawings in which FIGS. 1-4 schematically and in section show an embodiment of an anaesthesia-breathing apparatus according to the invention, FIG. 1 showing the parts of the apparatus in the position corresponding to the inhalation phase, FIG. 2 in the position corresponding to the initial portion of the exhalation phase, FIG. 3 in the position corresponding to the subsequent portion of the exhalation phase and FIG. 4 in the position corresponding to the pause between inhalation and exhalation, FIGS. 5 and 6 show in respectively longitudinal and transverse section schematically another embodiment of the anaesthesia-breathing apparatus according to the invention, and FIG. 7 schematically and in section shows another embodiment of the anaesthesia-breathing apparatus according to the invention.

DESCRIPTION OF THE PREFERRED EMBODIMENTS

Figure 1:
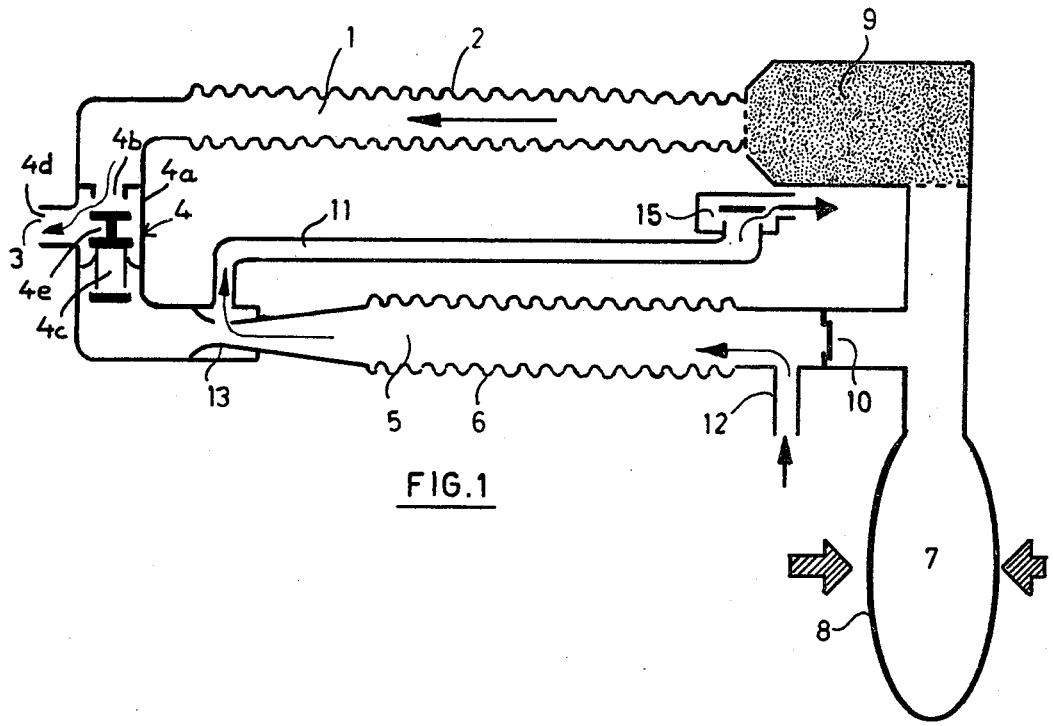

In the breathing apparatus according to FIGS. 1 to 4 the following apparatus parts can be distinguished:

A gas chamber 1 occupying the interior of a corrugated flexible hose 2 having stiff walls and rounded cross section is at the upstream end in open communication with a filter 9 for the absorption of carbon dioxide from recirculating breathing gas, said filter in turn at the upstream end being in communication with a conventional breathing bag 7 having an outer covering 8. It is to be noted that the filter 9 from a functional point of view is not a necessary part of the apparatus and that the position at which it is shown is not the only possible one.

At the downstream end the gas chamber 1 is in communication with a patient-connecting piece 3 via a control valve 4 which alternatively conducts exhaled gas either to one end of a recirculation gas chamber 5 or closes the communication to the recirculation gas chamber 5 and conducts the respiration gas from the gas chamber 1 to the patient.

The control valve 4 comprises a valve housing 4a having three connection ports 4b, 4c and 4d, port 4b leading to the gas chamber, port 4d into the patient connecting piece 3 and port 4c into the recirculation gas chamber 5. A valve device 4e may assume different opening or closing positions in cooperation with seats formed about ports 4b and 4c, valve element 4e in the one position during supply of respiration gas to the first port closing the communication from valve housing 4a to the other port 4c and simultaneously permitting the respiration gas supplied to flow via valve housing 4a to the third port 4d intended to communicate via connecting piece 3 with the respiratory ducts of the patient. When the pressure is discharged at the first port 4b valve device 4e is actuated by the pressure existing at the third port 4d due to a pressure increase in the lungs of the patient, so that the first port 4b is closed and the exhaled gas is conducted through valve housing 4a from the third port 4d and out through the second part 4c.

In the same way as in gas chamber 1 the greater part of the wall of the recirculation gas chamber 5 consists of a corrugated flexible hose 6 having stiff walls and rounded cross section. The chamber 5 at the upstream end is supplied with exhaled gas from the patient connecting piece 3 through the control valve 4 as described above, whereas the chamber 5 at the other end is in open communication with a connection 12 through which fresh gas is supplied from a pressurized source.

Close to control valve 4 the recirculation gas chamber 5 has the shape of a convergent-divergent duct in the most restricted portion 13 of which a side duct 11 is connected which at the opposite end is in communication with the atmosphere via an outwardly opening check valve 15.

At the end where the fresh-gas supply connection 12 opens into the recirculation gas chamber 5, chamber 5 is connected to the respiratory gas receptacle 7 or to the connection thereof with gas chamber 1. A check valve 10 opening towards the respiration gas receptacle, i.e. the respiration bag 7, is provided in the recirculation gas chamber 5 immediately downstream from the connection 12 for supplying fresh gas.

The apparatus described above operates as follows:

During the inflation phase illustrated in FIG. 1 the respiration bag 7 is compressed causing the check valve 10 to close the communication between the respiration bag and the recirculation gas chamber 5 so that gas from bag 7 flows through filter 9 and chamber 1 to the patient connecting piece 3 through the control valve housing 4a in which conditions are such that the communication with the recirculation gas chamber 5 is closed by valve device 4e.

Figure 2:
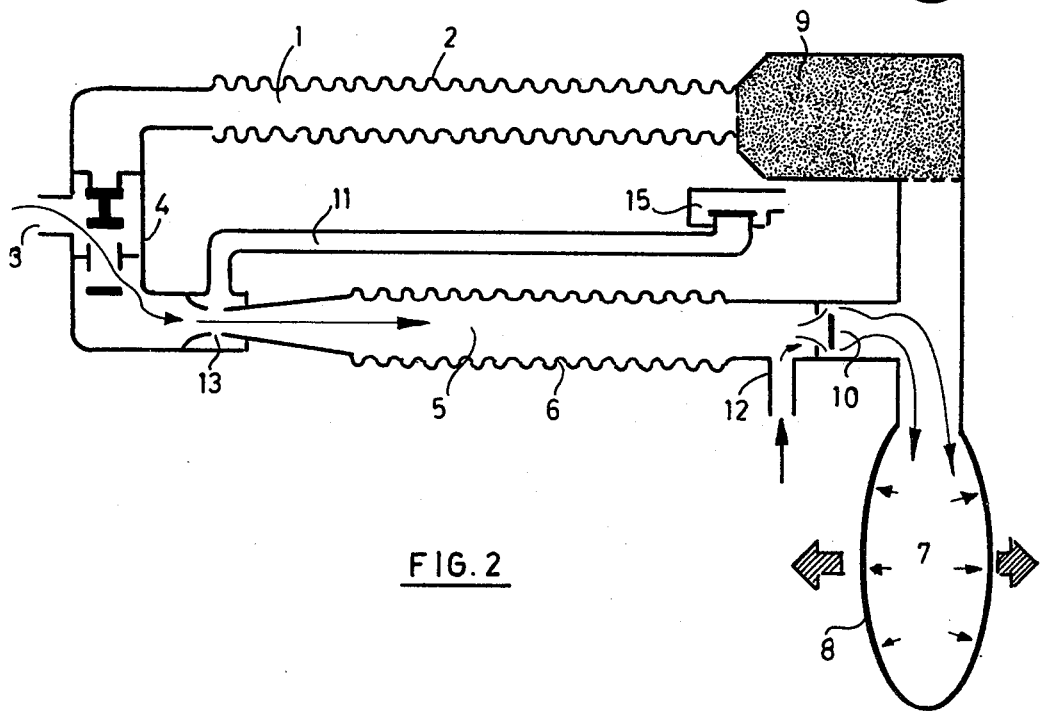
Figure 3:
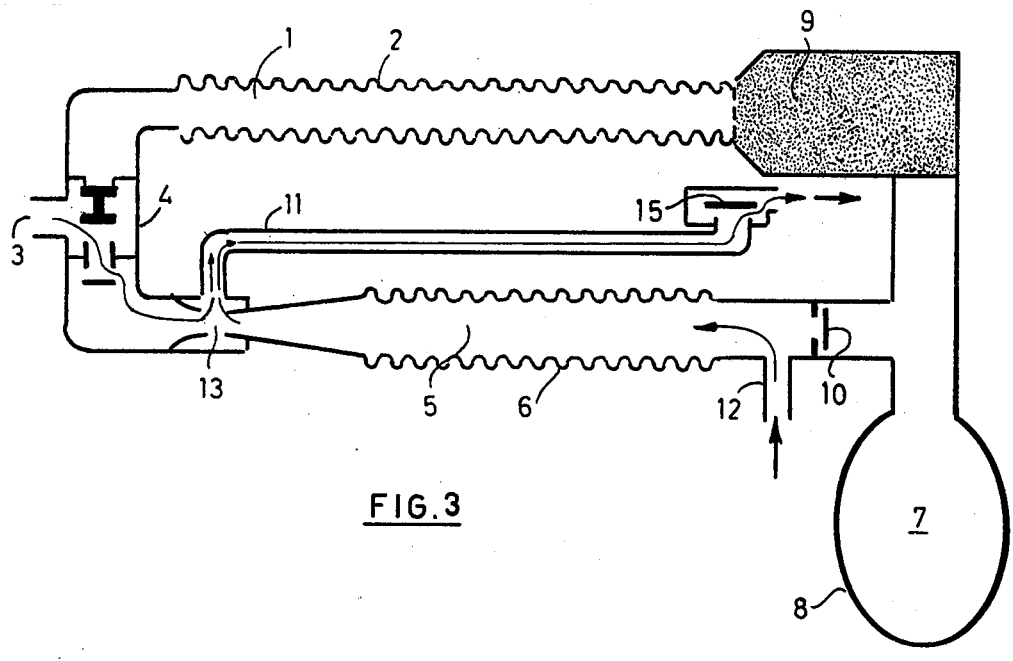

During the expiration phase, i.e. during the patient's exhalation, exhalation air will initially flow from the patient connecting piece 3 through the valve housing ports 4d and 4c into the recirculation gas chamber 5 while valve device 4e closes the communication with gas chamber 1 (FIG. 2). The exhalation gas, the greater part of which initially comprises unused gas, i.e. gas which has not been in contact with the lung alveoli of the patient, enters into the recirculation gas chamber 5 and flows together with newly supplied gas from connection 12 past check valve 10 into the respiration bag 7 which is in a stage of expansion. During the latter part of the expiration phase, after filling of the respiration bag 7 and balancing of the pressure in this bag in relation to the expiration pressure, the subsequently exhaled portion of the exhalation gas which predominantly comprises gas that has been in contact with the lung alveoli, will be discharged through side duct 11 and check valve 15 to the extent this gas is prevented from entering the recirculation gas chamber 5 due to the presence therein of previously received exhalation gas together with fresh gas supplied from connection 12. This latter part of the exhalation phase is illustrated in FIG. 3.

Figure 4:
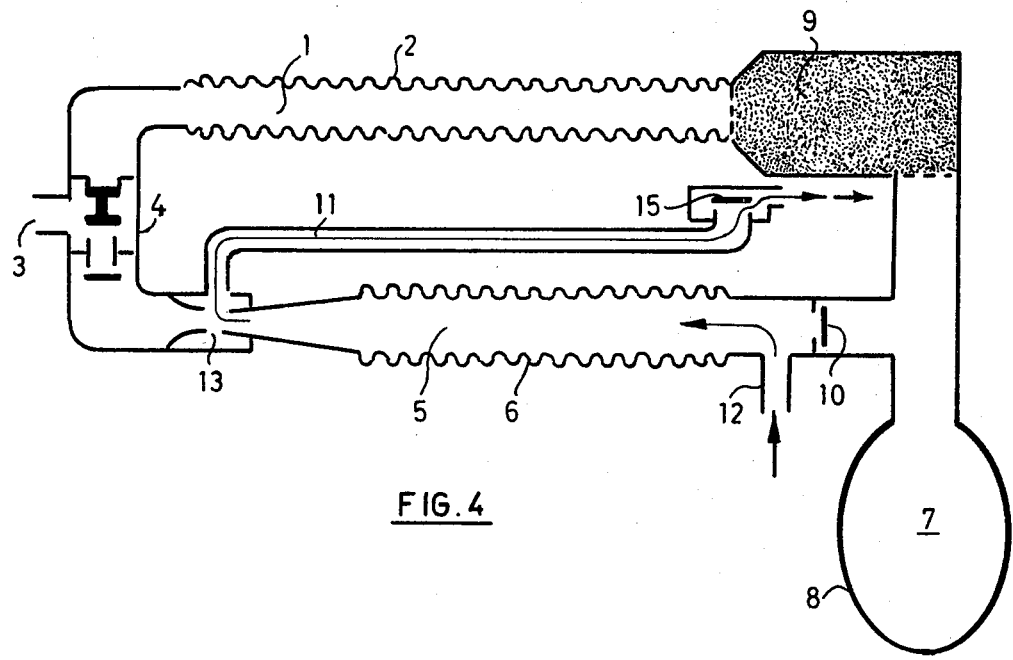

Finally, FIG. 4 shows the pause between the patient's exhalation and the subsequent inhalation phase initiated by renewed compression of the respiration bag 7. During this pause exhalation air previously received in the recirculation gas chamber 5 will be displaced by fresh gas supplied from connection 12. The gas supply is so adjusted that the gas leaving the side duct 11 through check valve 15 entirely or predominantly comprises used exhalation gas. From FIG. 1 it is seen that during the inhalation phase the expulsion of previously exhaled gas from the recirculation gas chamber 5 by fresh gas entering from connection 12 will continue, the inflow through connection 2 obviously being dimensioned in respect to the whole length of time during which there will be no outflow of gas from the recirculation gas chamber 5 to the respiration bag 7, i.e. the latter part of the exhalation phase (FIG. 3), the pause (FIG. 4) and the inhalation phase (FIG. 1).

In the construction according to FIGS. 5 and 6 a considerable constructive simplification is obtained by exploiting the fact that three parallel flow ducts, the gas chamber 1, the recirculation gas chamber 5 and the side duct 11 may be combined in such a way that one of the ducts, in the case of FIGS. 5 and 6 the side duct 11, is bounded by a thin-walled flexible casing enclosing the two other ducts, in the example shown gas chamber 1 and recirculation gas chamber 5, these two latter chambers consisting of hoses 2 and 6 respectively that may be corrugated and which have stiff, but flexible walls. These adjacent hoses 2 and 6 deform the casing 14 to an oval cross sectional shape, the cavities formed between the outer surfaces of the hoses and the casing constituting side duct 11 which connects recirculation gas chamber 5 via the first check valve 15 with the atmosphere.

In analogy to the embodiment according to FIGS. 5 and 6 it is possible that gas chamber 1 and side duct 11 are hoses of rounded cross section having stiff but flexible walls, for example corrugated hoses, which are enclosed in a flexible casing 14 with a thin wall, said casing being deformed by the two enclosed hoses into an oval cross sectional shape and connected in such a way with at least one of the enclosed ducts that the cavity formed between the outer surfaces of the hoses and the casing forms the recirculation gas chamber 5.

Figure 7:
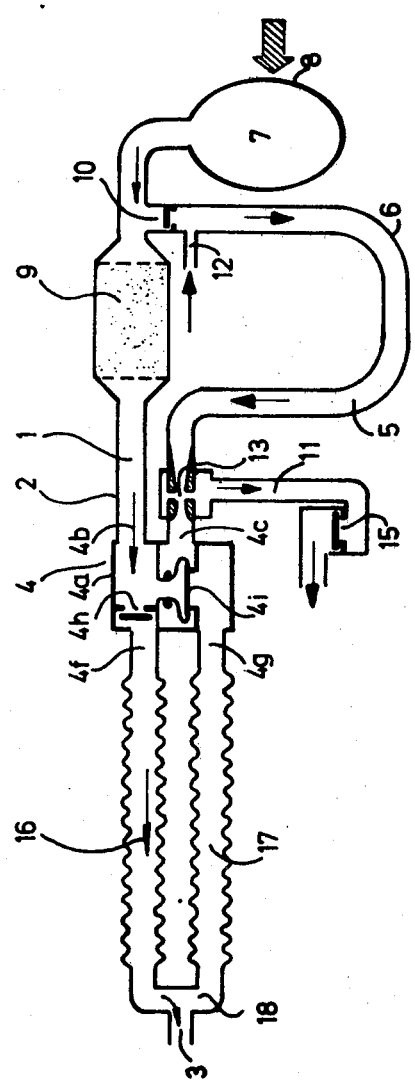

In the construction according to FIG. 7 the control valve 4 is connected with the patient connection piece 3 via a T-branch 18 and two extension hoses 16 and 17 enabling the comparatively large control valve 4 to be mounted where it is stationary and spaced from the patient. In the embodiment according to FIG. 7 the control valve 4 comprises a housing 4a having four communication ports 4b, 4c, 4f and 4g, out of which port 4b communicates with gas chamber 1, port 4c communicates with recirculation gas chamber 5 and ports 4f and 4g are respectively inlet and outlet connections with the patient connection piece 3 via extension hoses 16 and 17 respectively. The valve devices in the control valve 4 comprise a directional valve (check valve) 4h and a bellows valve 4i which upon the supply of respiration gas to the first port 4b permit flow through port 4f while simultaneously the bellows valve 4i closes communication from port 4g to port 4c. This condition is illustrated in FIG. 7. When the pressure in gas chamber 1 (and thereby in port 4b) is released the exhalation air (expiration gas) will be permitted to flow from port 4g outwardly through port 4c, while directional valve 4h closes the communication in a backward direction from extension hose 16 via port 4f. As for the rest, the embodiment according to FIG. 7 will operate in the same way as the two previously described embodiments.

What we claim is:

1. Anaesthesia-breathing apparatus for supplying gas to a patient, comprising:
    a first gas chamber having first and second ends;
    a second gas chamber having first and second ends, the first end of said second gas chamber being in the form of a convergent-divergent duct and the second end of said second gas chamber having an aperture therein for introducing fresh gas from a pressurized source, said second gas chamber holding a volume of gas which is at least equal to the volume of gas exhaled by a mature person which has been in contact with the lung alveoli;
    a side duct coupled to said second gas chamber at the most restricted portion of said convergent-divergent duct, said side duct being provided with a first check valve for discharging excess gas to the atmosphere;
    a patient connecting piece;
    a control valve coupled to the first ends of said first and second gas chambers and to said patient connecting piece, said valve alternately conducting gas exhaled by said patient through said connecting piece to said second gas chamber or conducting a mixture of exhaled gas and fresh gas from said first gas chamber to said connecting piece, said control valve blocking the flow of exhaled gas into said second gas chamber when said gas mixture is being conducted to said connecting piece from said first gas chamber;
    a respirator gas receptacle connected to the second ends of said first and second gas chambers; and
    a second check valve positioned in said second gas chamber between said aperture for introducing fresh gas and said respirator gas receptacle, said second check valve opening toward said respirator gas receptacle.

2. Anaesthesia-breathing apparatus as claimed in claim 1 wherein said control valve comprises a housing, first, second and third connection ports and a valve device, said first and second connection ports being coupled to the first ends of said first and second gas chambers respectively and said third connection port being coupled to said patient connecting piece, said valve device permitting a flow of gas under pressure from said first port to said third port while closing off communication from said housing to said second port, and, upon release of the pressure at said first port and an increase in pressure at said third port, closing said first port and permitting a flow of exhalation gas from said third port through said housing to said second port, the pressure at said third port resulting from a pressure increase in the lungs of the patient.

3. Anaesthesia-breathing apparatus as claimed in claim 1 wherein said first and second gas chambers are first and second flexible corregated hoses respectively having stiff walls and a rounded cross-section, and wherein said apparatus further comprises a thin-walled flexible casing surrounding said first and second hoses, said casing being deformed by said first and second enclosed hoses into an oval cross-sectional shape, the space between the outer surfaces of said hoses and the inner surface of said casing forming said side duct.

4. Anaesthesia-breathing apparatus as claimed in claim 1 wherein said first gas chamber and said side duct are first and second flexible corregated hoses respectively having stiff walls and a rounded cross-section, and wherein said apparatus further comprises a thin-walled flexible casing surrounding said first and second hoses, said casing being deformed by said first and second enclosed hoses into an oval cross-sectional shape, the space between the outer surfaces of said hoses and the inner surface of said casing forming said second gas chamber.

5. Anaesthesia-breathing apparatus as claimed in claim 1 wherein said control valve comprises a housing, first, second, third and fourth connection ports and first and second valve devices, said first and second connection ports being coupled to the first ends of said first and second gas chambers respectively and said third and fourth connection ports being coupled to said patient connecting piece, said first valve device opening to permit flow of gas under pressure from said first port to said third port while said second valve device closes off communication from said housing to said second port, and, upon release of the pressure at said first port and an increase in pressure at said third and fourth ports, said first valve device closes said third port while said second valve device opens to permit flow of exhalation gas from said fourth port through said housing to said second port, the pressure at said third and fourth ports resulting from the pressure increase in the lungs of the patient.

6. Anaesthesia-breathing apparatus as claimed in claim 5 which further comprises first and second extension hoses each having first and second ends, the first ends of said hoses being coupled to the third and fourth ports of said control valve respectively; and a T-shaped member having first and second arms coupled to the second ends of said first and second extension hoses and a third arm coupled to said patient connection piece, said extension arms allowing said control valve to be stationarily mounted at a distance from the patient.

7. Anaesthesia-breathing apparatus as claimed in claim 6 wherein said first valve device comprises a directional valve mounted in said third port and said second valve devices comprises a bellows valve mounted between said fourth and second ports, the opening and closing of said second valve device depending on the pressure in said first port and in said second extension hose.

8. Anaesthesia-breathing apparatus as claimed in claim 1 which further comprises a filter in series with said first gas chamber, said filter absorbing carbon dioxide from recirculating breathing gas.

* * * * *